US011555052B2

(12) United States Patent
Kwant

(10) Patent No.: US 11,555,052 B2
(45) Date of Patent: Jan. 17, 2023

(54) METHODS FOR PREVENTING DISULFIDE BOND REDUCTION IN CELL CULTURE HARVEST WITH SELENITE

(71) Applicant: BAYER HEALTHCARE LLC, Indianola, PA (US)

(72) Inventor: Kathryn Kwant, Oakland, CA (US)

(73) Assignee: Bayer HealthCare LLC, Whippany, NJ (US)

( * ) Notice: Subject to any disclaimer, the term of this patent is extended or adjusted under 35 U.S.C. 154(b) by 265 days.

(21) Appl. No.: 16/648,014

(22) PCT Filed: Sep. 26, 2018

(86) PCT No.: PCT/US2018/052798
§ 371 (c)(1),
(2) Date: Mar. 17, 2020

(87) PCT Pub. No.: WO2019/070468
PCT Pub. Date: Apr. 11, 2019

(65) Prior Publication Data
US 2020/0277329 A1 Sep. 3, 2020

Related U.S. Application Data

(60) Provisional application No. 62/566,817, filed on Oct. 2, 2017.

(51) Int. Cl.
| | |
|---|---|
| *C07K 1/14* | (2006.01) |
| *C07K 16/00* | (2006.01) |
| *C12P 21/00* | (2006.01) |
| *C07K 1/113* | (2006.01) |
| *C07K 16/06* | (2006.01) |

(52) U.S. Cl.
CPC ............ *C07K 1/1133* (2013.01); *C07K 1/145* (2013.01); *C07K 16/00* (2013.01); *C07K 16/065* (2013.01); *C12P 21/00* (2013.01); *C12N 2501/999* (2013.01)

(58) Field of Classification Search
CPC ...... C07K 1/1133; C07K 1/145; C07K 16/00; C12N 2501/00; C12N 2501/999; C12P 21/00; C12P 21/005; C12P 21/02
See application file for complete search history.

(56) References Cited

U.S. PATENT DOCUMENTS

| | | |
|---|---|---|
| 8,574,869 B2 | 11/2013 | Kao et al. |
| 2002/0032315 A1 | 3/2002 | Baca et al. |
| 2004/0029229 A1 | 2/2004 | Reeves et al. |
| 2006/0194280 A1 | 8/2006 | Dillon et al. |
| 2009/0053786 A1 | 2/2009 | Kao et al. |
| 2011/0250644 A1* | 10/2011 | Ling .................... C07K 16/244 435/404 |
| 2015/0275259 A1 | 10/2015 | Inoue |

FOREIGN PATENT DOCUMENTS

| | | |
|---|---|---|
| AU | 2013203411 C1 | 1/2017 |
| EP | 2586788 A1 | 5/2013 |
| WO | 2009009523 A2 | 1/2009 |

OTHER PUBLICATIONS

Chung; et al., "Effects of antibody disulfide bond reduction on purification process performance and final drug substance stability: Effects of Antibody Disulfide Bond Reduction", Biotechnology and Bioengineering, vol. 114 No. 6, 1264-1274, (2017).
Davydov; et al., "A Superoxo-Ferrous State in a Reduced Oxy-Ferrous Hemoprotein and Model Compounds", Journal of the American Chemical Society, vol. 125 No. 52, 16340-16346, (2003).
Hu; et al., "Selenium as a sulfhydryl redox catalyst and survey of potential selenium-dependent enzymes", Journal of Inorganic Biochemistry, vol. 30 No. 3, 239-248, (1987).
Hutterer; et al., "Monoclonal Antobody Disulfide Reduction During Manufacturing: Untangling Process Effects from Product Effects", Landes Bioscience, vol. 5 No. 4, 608-613, (2013).
"International Search Report & Written Opinion of International Application No. PCT/US2018/052798 dated Jan. 18, 2019".
"International Search Report & Written Opinion of International Application No. PCT/US2018/052800 dated Nov. 28, 2018".
Kao; et al., "Mechanism of Antibody Reduction in Cell Culture Production Processes", Biotechnology and Bioengineering, Nov. 1, 2010, vol. 107 Issue No. 4, 622-632.
Li; et al., "Aggregation and Precipitation of Human Relaxin Induced by Metal-Catalyzed Oxidation", Biochemistry, vol. 34 No. 17, 5762-5772, (1995).
Li; et al., "Low level formation of potent catalytic IgG fragments mediated by disulfide bond instability", Molecular Immunology, vol. 33 No. 7/8, 593-600, (1996).
Li; et al., "Metal-Leachate-Induced Conjugate Protein Instability", Journal of Pharmaceutical Sciences, vol. 101 No. 8, 2733-2743, (2012).
Rachmilovich-Calis; et al., "New mechanistic aspects of the fenton reaction", Chemistry—A European Journal, vol. 15 No. 33, 8303-8309, (2009).
Rasnoshik; et al., "Reduction of ethylene by Ni(1 )(cyclam)(+) in aqueous solutions", Journal of Physical Chemistry A, vol. 112 No. 50, 12769-1277, (2008).
Rudiuk., "Importance of the dynamics of adsorption and of a transient interfacial stress on the formation of aggregates of IgG antibodies", The Royal Society of Chemistry, Soft Matter. vol. 8, 2651-2661 (2012).
Rustandi; et al., "Use of CE-SDS gel for characterization of monoclonal antibody hinge region clipping due to copper and high pH stress", Electrophoresis, vol. 32, 3078-3084, (2011).

(Continued)

*Primary Examiner* — Jeffrey E. Russel
(74) *Attorney, Agent, or Firm* — Bayer HealthCare LLC

(57) ABSTRACT

This disclosure relates to methods for the prevention of the reduction of disulfide bonds in a polypeptide expressed in a recombinant host cell, comprising, following fermentation, adding selenite and/or its salts or derivatives to a harvest solution of the recombinant host cell, wherein the disulfide bond in the polypeptide remains non-reduced.

11 Claims, 3 Drawing Sheets

(56) References Cited

OTHER PUBLICATIONS

Wiesbauer; et al., "Renewal of the Air-Water Interface as a Critical System Parameter of Protein Stability Aggregation of the Human Growth Hormone and Its Prevention by Surface-Active Compounds", Langmuir, vol. 29 No. 49, 15240-15250, (2013).

Yan; et al., "Breaking the Light and Heavy Chain Linkage of Human Immunoglobulin G1 (IgG1) by Radical Reactions", Journal of Biological Chemistry, vol. 286 No. 28, 24674-24684, (2011).

"Search Report and Written Opinion for Corresponding Singapore Application 11202002009P dated Sep. 3, 2021".

"Extended European Search Report for corresponding EP Application No. 22160394.7 dated Sep. 20, 2022".

Kumar; Sushil et al, "Selenite is a substrate for calf thymus thioredoxin reductase and thioredoxin and elicits a large non-stoichiometric oxidation of NADPH in the presence of oxygen", European Journal of Biochemistry, Jul. 1, 1992, vol. 207 No. 2, 435-439.

M'Hu; &. A. L. Tappel., "Selenium as a sulfhydryl redox catalyst and survey of potential selenium-dependent enzymes", Journal of Inorganic Biochemistry, 1987, vol. 30 No. 3, 239-248.

\* cited by examiner

METHODS FOR PREVENTING DISULFIDE BOND REDUCTION IN CELL CULTURE HARVEST WITH SELENITE

BACKGROUND

The biopharmaceutical industry produces a variety of therapeutic proteins using cell culture. A variety of cell types, including both prokaryotes and eukaryotes, can be used to express a recombinant therapeutic protein. The biopharmaceutical industry relies heavily on mammalian cells due to their ability to produce properly folded and post-translationally modified proteins. Manufacturing a therapeutic protein typically begins by culturing cells in a bioreactor. Various nutrients and process parameters are monitored to ensure optimal cell growth and protein production. The therapeutic protein is typically secreted, so the first step in harvesting the protein is to remove the cells. In the bioreactor and during cell removal, cells may lyse, releasing components that may alter or degrade the recombinant protein. For example, enzymes and other components in the harvest may reduce disulfide bonds. Because intact disulfide bonds are critical for maintaining protein structure and function, methods to prevent disulfide reduction are of great interest.

SUMMARY

The embodiments provide a method for the prevention of the reduction of disulfide bonds in a polypeptide expressed in a recombinant host cell, comprising, following fermentation, adding selenite, its salts and/or derivatives, to a harvest solution of the recombinant host cell, wherein the disulfide bond in the polypeptide remains non-reduced.

BRIEF DESCRIPTION OF THE DRAWINGS

The skilled artisan will understand that the drawings, described below, are for illustration purposes only. The drawings are not intended to limit the scope of the present teachings or claims in any way.

DETAILED DESCRIPTION

Figure 1:
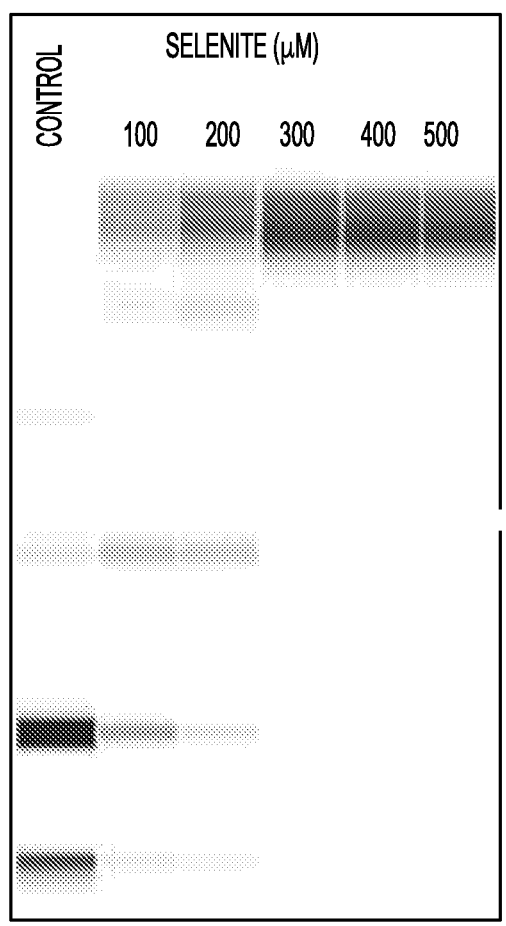
FIG. 1 shows a Disulfide reduction assay using project 1 harvest (CHOK1-SV cells expressing IgG2) and varying concentrations of sodium selenite, pH 7.0.

This disclosure provides for methods which relate to the prevention of disulfide bond reduction of polypeptides.

Definitions

Whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended (for example in the document where the term is originally used). The use of "or" means "and/or" unless stated otherwise. The use of "a" herein means "one or more" unless stated otherwise or where the use of "one or more" is clearly inappropriate. The use of "comprise," "comprises," "comprising," "include," "includes," and "including" are interchangeable and are not limiting. For example, the term "including" shall mean "including, but not limited to."

The term "TFPI" as used herein refers to any variant, isoform, and/or species homolog of TFPI in its form that is naturally expressed by cells and present in plasma.

The term "TFPI" as used herein refers to an activated form of TFPI as used herein, an "antibody" refers to a whole antibody and any antigen binding fragment (i.e., "antigen-binding portion") or single chain thereof. The term includes a full-length immunoglobulin molecule (e.g., an IgG antibody) that is naturally occurring or formed by normal immunoglobulin gene fragment recombinatorial processes, or an immunologically active portion of an immunoglobulin molecule, such as an antibody fragment, that retains the specific binding activity. Regardless of structure, an antibody fragment binds with the same antigen that is recognized by the full-length antibody. For example, an anti-TFPI monoclonal antibody fragment binds to an epitope of TFPI. The antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and VH domains of a single arm of an antibody, (v) a dAb fragment (Ward et al., (1989) Nature 341:544-546), which consists of a VH domain; (vi) an isolated complementarity determining region (CDR); (vii) minibodies, diaboidies, triabodies, tetrabodies, and kappa bodies (see, e.g. Ill et al., Protein Eng 1997; 10:949-57); (viii) camel IgG; and (ix) IgNAR. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al (1988) Proc. Natl. Acad. Sci. USA 85:5879-5883). Such single chain antibodies are also intended to be encompassed within the term "antigen-binding portion" of an antibody. These antibody fragments are obtained using conventional techniques known to those with skill in the art, and the fragments are analyzed for utility in the same manner as are intact antibodies.

Furthermore, it is contemplated that an antigen binding fragment can be encompassed in an antibody mimetic. The term "antibody mimetic" or "mimetic" as used herein is meant as a protein that exhibits binding similar to an antibody but is a smaller alternative antibody or a non-antibody protein. Such antibody mimetic can be comprised in a scaffold. The term "scaffold" refers to a polypeptide platform for the engineering of new products with tailored functions and characteristics.

As used herein, the term "anti-TFPI antibody" refers to an antibody that specifically binds to an epitope of and its heparin associated complex. When bound in vivo to an epitope of TFPI, the anti-TFPI antibodies disclosed herein augment one or more aspects of the blood clotting cascade.

As used herein, the terms "inhibits binding" and "blocks binding" (e.g., referring to inhibition/blocking of binding of TFPI substrate to TFPI) are used interchangeably and encompass both partial and complete inhibition or blocking of a protein with its substrate, such as an inhibition or blocking by at least about 10%, about 20%, about 30%, about 40%, about 50%, about 60%, about 70%, about 80%, about 90%, about 95%, about 96%, about 97%, about 98%, about 99%, or about 100%. As used herein, "about" means+/−10% of the numerical value indicated.

In reference to the inhibition and/or blocking of binding of TFPI substrate to TFPI, the terms inhibition and blocking also include any measurable decrease in the binding affinity of TFPI to a physiological substrate when in contact with an anti-TFPI antibody as compared to TFPI not in contact with an anti-TFPI antibody, e.g., the blocking of the interaction of TFPI with its substrates by at least about 10%, about 20%, about 30%, about 40%, about 50%, about 60%, about 70%, about 80%, about 90%, about 95%, about 96%, about 97%, about 98%, about 99%, or about 100%.

The terms "monoclonal antibody" or "monoclonal antibody composition" as used herein refers to a preparation of antibody molecules of single molecular composition. A monoclonal antibody composition displays a single binding specificity and affinity for a particular epitope. Accordingly, the term "human monoclonal antibody" refers to antibodies displaying a single binding specificity that have variable and constant regions derived from human germline immunoglobulin sequences. The human antibodies can include amino acid residues not encoded by human germline immunoglobulin sequences (e.g., mutations introduced by random or site-specific mutagenesis in vitro or by somatic mutation in vivo).

An "isolated antibody," as used herein, is intended to refer to an antibody which is substantially free of other biological molecules, including antibodies having different antigenic specificities (e.g., an isolated antibody that binds to TFPI is substantially free of antibodies that bind antigens other than TFPI). In some embodiments, the isolated antibody is at least about 75%, about 80%, about 90%, about 95%, about 97%, about 99%, about 99.9% or about 100% pure by dry weight. In some embodiments, purity can be measured by a method such as column chromatography, polyacrylamide gel electrophoresis, or HPLC analysis. An isolated antibody that binds to an epitope, isoform or variant of human TFPI can, however, have cross-reactivity to other related antigens, e.g., from other species (e.g., TFPI species homologs). Moreover, an isolated antibody can be substantially free of other cellular material and/or chemicals. As used herein, "specific binding" refers to antibody binding to a predetermined antigen. Typically, an antibody that exhibits "specific binding" binds to an antigen with an affinity of at least about $10^{-5}$M and binds to that antigen with an affinity that is higher, for example at least two-fold greater, than its binding affinity for an irrelevant antigen (e.g., BSA, casein). The phrases "an antibody recognizing an antigen" and "an antibody specific for an antigen" are used interchangeably herein with the term "an antibody which binds specifically to an antigen." As used herein, the term "minimal binding" refers to an antibody that does not bind to and/or exhibits low affinity to a specified antigen. Typically, an antibody having minimal binding to an antigen binds to that antigen with an affinity that is lower than about $10^2$ $M^{-1}$ and does not bind to a predetermined antigen with higher affinity than it binds to an irrelevant antigen.

As used herein, the term "high affinity" for an antibody, such as an IgG antibody refers to a binding affinity of at least about $10^{-7}$M, in at least one embodiment at least about $10^{-8}$M, in some embodiments at least about $10^9 M^{-1}$, $10^{10}$ $M^{-1}$, $1011 M^{-1}$ or greater, e.g., up to $10^{12} M^{-1}$ or greater. However, "high affinity" binding can vary for other antibody isotypes. For example, "high affinity" binding for an IgM isotype refers to a binding affinity of at least about $10^7 M^{-1}$.

As used herein, "isotype" refers to the antibody class (e.g., IgM or IgG1) that is encoded by heavy chain constant region genes.

"Complementarity-determining region" or "CDR" refers to one of three hypervariable regions within the variable region of the heavy chain or the variable region of the light chain of an antibody molecule that form the N-terminal antigen-binding surface that is complementary to the three-dimensional structure of the bound antigen. Proceeding from the N-terminus of a heavy or light chain, these complementarity-determining regions are denoted as "CDR1," "CDR2," and "CDR3," respectively [Wu T T, Kabat E A, Bilofsky H, Proc Natl Acad Sci USA. 1975 December; 72(12):5107 and Wu T T, Kabat E A, J Exp Med. 1970 Aug. 1; 132(2):211]. CDRs are involved in antigen-antibody binding, and the CDR3 comprises a unique region specific for antigen-antibody binding. An antigen-binding site, therefore, can include six CDRs, comprising the CDR regions from each of a heavy and a light chain V region. The term "epitope" refers to the area or region of an antigen to which an antibody specifically binds or interacts, which in some embodiments indicates where the antigen is in physical contact with the antibody. Conversely, the term "paratope" refers to the area or region of the antibody on which the antigen specifically binds. Epitopes characterized by competition binding are said to be overlapping if the binding of the corresponding antibodies are mutually exclusive, i.e. binding of one antibody excludes simultaneous binding of another antibody. The epitopes are said to be separate (unique) if the antigen is able to accommodate binding of both corresponding antibodies simultaneously.

The term "competing antibodies," as used herein, refers to antibodies that bind to about, substantially or essentially the same, or even the same, epitope as an antibody against TFPI as described herein. "Competing antibodies" include antibodies with overlapping epitope specificities. Competing antibodies are thus able to effectively compete with an antibody as described herein for binding to TFPI. In some embodiments, the competing antibody can bind to the same epitope as the antibody described herein. Alternatively viewed, the competing antibody has the same epitope specificity as the antibody described herein.

As used herein, "conservative substitutions" refers to modifications of a polypeptide that involve the substitution of one or more amino acids for amino acids having similar biochemical properties that do not result in loss of a biological or biochemical function of the polypeptide. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine), and aromatic side chains (e.g., tyrosine, phenylalanine, tryptophan, histidine).

Antibodies of the present disclosure can have one or more conservative amino acid substitutions yet retain antigen binding activity.

For nucleic acids and polypeptides, the term "substantial homology" indicates that two nucleic acids or two polypeptides, or designated sequences thereof, when optimally aligned and compared, are identical, with appropriate nucleotide or amino acid insertions or deletions, in at least about 80% of the nucleotides or amino acids, usually at least about 85%, in some embodiments about 90%, 91%, 92%, 93%, 94%, or 95%, in at least one embodiment at least about 96%, 97%, 98%, 99%, 99.1%, 99.2%, 99.3%, 99.4%, or 99.5% of the nucleotides or amino acids. Alternatively, substantial homology for nucleic acids exists when the segments will hybridize under selective hybridization conditions to the complement of the strand. Also included are nucleic acid sequences and polypeptide sequences having substantial homology to the specific nucleic acid sequences and amino acid sequences recited herein. The percent identity between two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, such as without limitation the AlignX™ module of VectorNTI™ (Invitrogen Corp., Carlsbad, Calif.). For AlignX™, the default parameters of multiple alignment are: gap opening penalty: 10; gap extension penalty: 0.05; gap separation penalty range: 8; % identity for alignment delay: 40.

The percent identity between two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, such as without limitation the AlignX™ module of VectorNTI™ (Invitrogen Corp., Carlsbad, Calif.). For AlignX™, the default parameters of multiple alignment are: gap opening penalty: 10; gap extension penalty: 0.05; gap separation penalty range: 8; % identity for alignment delay: 40.

Another method for determining the best overall match between a query sequence (a sequence of the present disclosure) and a subject sequence, also referred to as a global sequence alignment, can be determined using the CLUSTALW computer program (Thompson et al., Nucleic Acids Research, 1994, 2(22): 4673-4680), which is based on the algorithm of Higgins et al., (Computer Applications in the Biosciences (CABIOS), 1992, 8(2): 189-191). In a sequence alignment the query and subject sequences are both DNA sequences. The result of said global sequence alignment is in percent identity. Parameters that can be used in a CLUSTALW alignment of DNA sequences to calculate percent identity via pairwise alignments are: Matrix=IUB, k-tuple=1, Number of Top Diagonals=5, Gap Penalty=3, Gap Open Penalty=10, Gap Extension Penalty=0.1. For multiple alignments, the following CLUSTALW parameters can be used: Gap Opening Penalty=10, Gap Extension Parameter=0.05; Gap Separation Penalty Range=8; % Identity for Alignment Delay=40.

The nucleic acids can be present in whole cells, in a cell lysate, or in a partially purified or substantially pure form. A nucleic acid is "isolated" or "rendered substantially pure" when purified away from other cellular components with which it is normally associated in the natural environment. To isolate a nucleic acid, standard techniques such as the following can be used: alkaline/SDS treatment, CsCl banding, column chromatography, As used herein, the term "about" refers to +/−10% of the unit value provided.

As used herein, the term "substantially" refers to the qualitative condition of exhibiting a total or approximate degree of a characteristic or property of interest. One of ordinary skill in the biological arts will understand that biological and chemical phenomena rarely, if ever, achieve or avoid an absolute result because of the many variables that affect testing, production, and storage of biological and chemical compositions and materials, and because of the inherent error in the instruments and equipment used in the testing, production, and storage of biological and chemical compositions and materials. The term "substantially" is, therefore, used herein to capture the potential lack of completeness inherent in many biological and chemical phenomena.

Example 1—Materials

Cell culture fluid was produced using standard manufacturing procedures. Briefly, CHO cells expressing an antibody were cultured in shake flasks until sufficient cell numbers were reached to inoculate a 2 L or 5 L glass stirred tank bioreactor. After inoculation, dissolved oxygen, pH, temperature, and agitation rate were controlled and daily samples were analyzed to ensure accuracy. A concentrated nutrient feed was added continuously starting 2 days after inoculation and a solution of glucose was added as needed to provide sufficient nutrients. Cell culture fluid was harvested 14 days after inoculation. All reagents were obtained from Sigma Aldrich unless otherwise stated. MabSelect Sure resin was obtained from GE Healthcare Life Sciences.

Example 2—Small Scale Reduction Assay

Harvested cell culture fluid was placed into a glove bag (Atmosbag, Sigma) filled with nitrogen. 40 mL of the harvest was poured into 50 mL conical tubes on ice and chilled for 20 min. The harvest was then sonicated on ice (Sonic Dismembrator Model 100, Fisher Scientific) for 60 seconds at power 3. This setting resulted in approximately 99% cell lysis. The conical tubes were tightly closed, brought out of the bag, and centrifuged for 15 minutes at 4000×g. The tubes were then brought back into the bag and re-purged with nitrogen. Lysed cell supernatant was filtered with 0.45 um sterile filters (Milipore) and transferred to a 96 deep-well plate. The lysed cell supernatant was incubated at room temperature without exposure to oxygen. At each time point, a 200 uL sample was quenched with 17.4 uL 250 mM NEM to cap all free thiols. Quenched samples were stored at 4 C until purification and/or analysis. To test inhibitors, a stock solution of 3 M sodium selenite, pH 7.0 was added to the lysed cell supernatant at the beginning of incubation to achieve concentrations ranging from 0 to 190 mM. Samples were taken and quenched at 0, 24, and 48 hours after addition of inhibitor.

Example 3—Batch Protein a Purification

Antibody was purified from harvested cell culture fluid using MabSelect Sure affinity resin. The equilibration buffer was 50 mM Tris, 50 mM NaCl, pH 7.0. The wash buffer was 50 mM Sodium acetate, 1 M NaCl, pH 5.2. The elution buffer was 50 mM Sodium Acetate, pH 3.7 and the neutralization buffer was 1M Tris, pH 8.0. In a 96 well filter plate, 20 uL of resin slurry (50% v/v in equilibration buffer) was combined with 170 uL quenched harvested cell culture fluid. The plate was incubated for 30 min then centrifuged with a 96 well plate underneath to catch the flow-through, which was discarded. All centrifugation steps were performed for 10 minutes at 4000×g. The resin was washed with 120 uL wash buffer, centrifuged, then washed with 120 uL equilibration buffer and centrifuged again. After the two wash steps, 50 uL elution buffer was added to the filter plate and incubated for 3 min. A clean 96 well plate was prepped with 28 uL neutralization buffer and used to collect the eluate. The antibody solution was mixed by pipetting up and down, then stored at −70° C. until analysis.

Example 4—Caliper Assay

Capillary electrophoresis measurements were acquired with the Caliper LabChip GX II. Sample preparation was carried out according to the manufacturer's instructions. Digital gel-like images were generated using the LabChip GX software.

Reduction was studied by fully lysing harvested cell culture fluid in an oxygen free environment. This maximized the release of intracellular reducing components, minimized oxygen interference, and prevented re-oxidation of disulfides by oxygen. This allowed the reduction inhibitor to be tested under the "worst-case" or most reducing conditions possible. Antibody disulfide reduction was monitored over time by purifying the antibody from the lysed cell fluid and analyzing it using non-reduced capillary electrophoresis, which separates proteins based on size and is able to detect interchain disulfide bond breakage.

Figure 2:
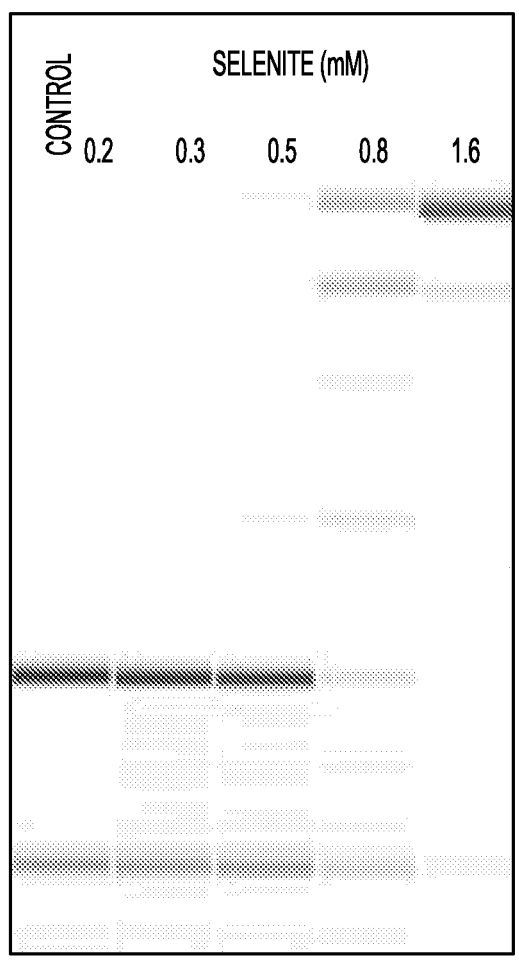
FIG. 2 shows a Disulfide reduction assay using project 2 harvest (CHO-M Cells expressing an IgG1) and varying concentrations of sodium selenite, pH 7.0.

To test the effectiveness of selenite for preventing disulfide reduction, various concentrations of sodium selenite were added to anaerobic lysed cell culture harvest of project 1 (CHOK1-SV cell expressing an IgG2) and project 2 (CHOK1-SV cell expressing an IgG2) and the results are shown in FIG. 1 and FIG. 2. The minimum concentration of selenite to prevent reduction for 24 hours is between 0.2 and 0.3 mM for project 1 and between 0.8 and 1.6 mM for project 2. Higher concentrations of selenite were required to prevent reduction for project 2. This could be due to IgG1 molecules being more susceptible to reduction than IgG2 molecules or differences in the expression of reducing enzymes in the two cell lines. This assay measured the concentration of inhibitor required under the most reducing conditions (all intracellular reducing components were released and no oxygen was introduced). Lower concentrations may be sufficient to prevent reduction under more realistic clarified harvest conditions. Higher concentrations of selenite are also effective.

Remarkably it was discovered that antibody disulfide reduction was prevented by the addition of sodium selenite to the harvested cell culture fluid (HCCF). Selenite is a substrate for Thioredoxin reductase and Glutathione reductase, two intracellular enzymes that may contribute to antibody reduction. Both enzymes required NADPH to reduce disulfides. The selenite may act as a decoy substrate. The enzymes would, therefore, theoretically reduce selenite and deplete the supply of NADPH before antibody reduction can occur.

Example 5—Experiments

Experiment 1

Figure 3:
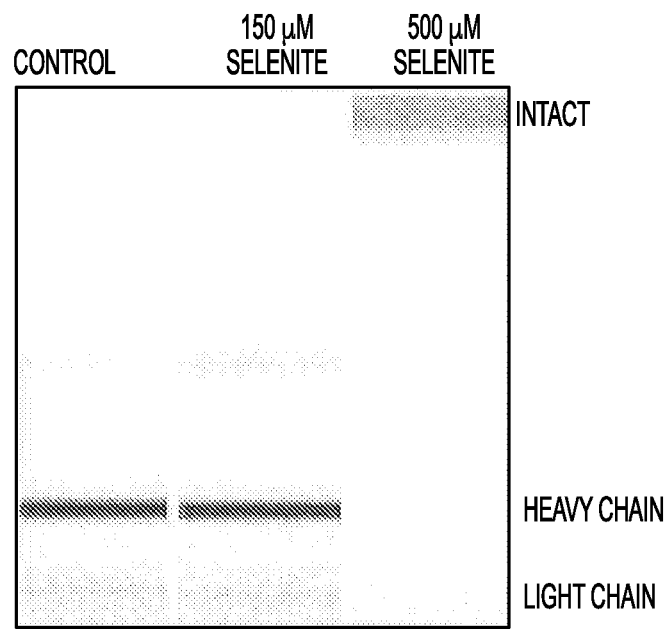
FIG. 3 shows the results of a first experiment conducted using a TFPI harvest and minimal lysing of cells.

TFPI cell culture harvest was clarified using depth filters. A concentrated solution of sodium selenite was added to the resulting cell free harvest to achieve concentrations of 0, 150, and 500 uM (See FIG. 3). The harvest was then held under nitrogen (to prevent oxygen inhibition) for 24 hours. After the nitrogen hold, the antibody was purified and disulfide reduction was analyzed using capillary electrophoresis. Reduction was prevented by 500 uM selenite, but not 150 uM selenite.

Experiment 2

Figure 4:
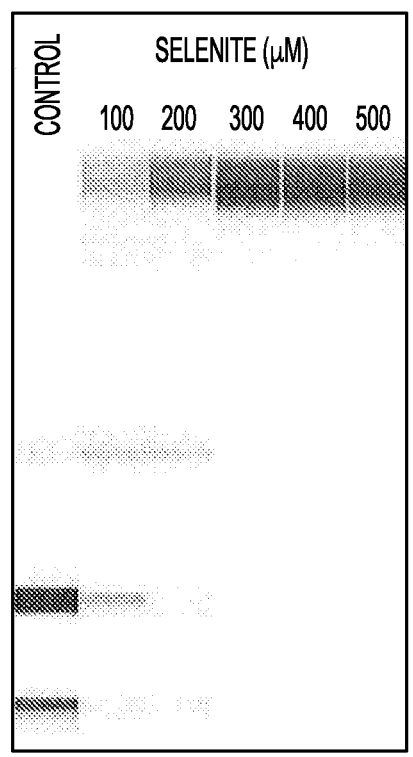
FIG. 4 shows the results of a second experiment conducted using a TFPI harvest and fully lysed cells.

TFPI cell culture harvest was lysed under nitrogen using a sonicator. The cell debris was removed then a concentrated solution of sodium selenite was added to achieve selenite concentrations between 0 and 500 uM (See FIG. 4). The samples were stored under nitrogen for 48 hours. The antibody was then purified and disulfide reduction was analyzed using capillary electrophoresis. Reduction was completely prevented by 300 uM selenite, but not by 200 uM selenite. The required concentration is therefore between 200 and 300 uM under these harvest conditions. The major difference between the experiments (other than the concentrations of selenite tested): Experiment 1 was done with TFPI harvest that was clarified using depth filters, and held for 24 hours. Minimal cell lysis should occur during this clarification. Experiment 2 was done with TFPI harvest where the cells had all been fully lysed, releasing all internal components that may contribute to reduction, and held for 48 hours. This is the worst case scenario for antibody reduction. Selenite was still effective at preventing reduction in this worst case scenario.

The embodiments provide for the possible use of various selenite solutions. For instance, the selenite solution can comprise calcium selenite, sodium selenite, potassium selenite, etc. It should be effective with proteins produced in mammalian cells, bacteria, yeast, etc. It should be effective for any protein with disulfide bonds, not just antibodies. Selenite improves over other methods to prevent reduction (adding metals, adding glutathione, air/$O_2$ sparging, etc.), because it does not require special equipment and is unlikely to impact product stability. Adding metals to prevent reduction may negatively impact antibody stability by inducing protein precipitation (Li, Osborne et al. 2012), oxidation (Li, Nguyen et al. 1995; Masaraw et al. 2009), and/or cleavage (Rustandi and Wang 2001, Yan and Boyd 2011). Sparging harvest with air or oxygen may increase protein denaturation and/or aggregation at the air-liquid interface (Wiesbauer et al. 2013; Rudik et al. 2012). Also, specialized harvest tanks are required for harvest sparging. Oxidized glutathione, once reduced by components in the harvest, then has the potential to reduce disulfide bonds or oxidizing agents.

While the present embodiments have been described with reference to the specific embodiments and examples, it should be understood that various modifications and changes can be made and equivalents can be substituted without departing from the true spirit and scope of the claims appended hereto. The specification and examples are, accordingly, to be regarded in an illustrative rather than in a restrictive sense. Furthermore, the disclosure of all articles, books, patent applications and patents referred to herein are incorporated herein by reference in their entireties.

I claim:

1. A method for the prevention of the reduction of disulfide bond in a polypeptide expressed in a recombinant host cell, comprising, following fermentation, adding selenite to a harvest solution of the recombinant host cell, wherein the disulfide bond in the polypeptide remains non-reduced.

2. The method of claim 1, wherein the polypeptide comprises an antibody.

3. The method of claim 1, wherein the polypeptide comprises a biologically functional fragment of an antibody.

4. The method of claim 1, wherein the host cell comprises a eukaryotic cell.

5. The method of claim 4, wherein the eukaryotic cell comprises a mammalian cell.

6. The method of claim 5, wherein the mammalian cell comprises a Chinese Hamster Ovary (CHO) cell.

7. A method as recited in claim 1, wherein the selenite is:
   (a) added in a concentration between 0.01-100 millimolar; or
   (b) added in a concentration between 0.1-10 millimolar.

8. The method of claim 1, wherein the selenite comprises a selenite salt selected from the group consisting of calcium selenite, sodium selenite, and potassium selenite.

9. A method as recited in claim 1, wherein the polypeptide comprises an IgG antibody.

10. A method as recited in claim 9, wherein the IgG antibody comprises an IgG2.

11. A method as recited in claim 9, wherein the IgG antibody comprises an IgG1.

* * * * *